(12) United States Patent
O'Neil et al.

(10) Patent No.: US 7,226,456 B2
(45) Date of Patent: Jun. 5, 2007

(54) TRACKABLE MEDICAL TOOL FOR USE IN IMAGE GUIDED SURGERY

(75) Inventors: Michael O'Neil, West Barnstable, MA (US); Paul Joseph Birkmeyer, Marshfield, MA (US); Spanky Allen Raymond, Uniontown, OH (US)

(73) Assignee: Depuy Acromed, Inc., Raynham, MA (US)

( * ) Notice: Subject to any disclaimer, the term of this patent is extended or adjusted under 35 U.S.C. 154(b) by 443 days.

(21) Appl. No.: 10/334,466

(22) Filed: Dec. 31, 2002

(65) Prior Publication Data
US 2004/0127888 A1 Jul. 1, 2004

(51) Int. Cl.
*A61B 19/00* (2006.01)

(52) U.S. Cl. .................. 606/130; 600/429; 600/417

(58) Field of Classification Search .................. 606/79, 606/80, 86, 130, 131, 170, 172, 173, 180; 600/424, 587; 340/539.13; 81/436–461, 81/58–63.2; 279/118
See application file for complete search history.

(56) References Cited

U.S. PATENT DOCUMENTS

| | | | |
|---|---|---|---|
| 4,352,354 A * | 10/1982 | Ujihara | 604/272 |
| 5,207,681 A | 5/1993 | Ghadjar et al. | |
| 5,474,558 A | 12/1995 | Neubardt | |
| 5,645,545 A | 7/1997 | Bryant | |
| 5,682,890 A | 11/1997 | Kormos et al. | |
| 5,732,703 A | 3/1998 | Kalfas et al. | |
| 5,772,594 A | 6/1998 | Barrick | |
| 6,021,343 A * | 2/2000 | Foley et al. | 600/429 |
| 6,179,512 B1 * | 1/2001 | Gibson et al. | 403/374.1 |
| 6,190,395 B1 | 2/2001 | Williams | |

FOREIGN PATENT DOCUMENTS

| WO | WO 96/11624 A2 | 4/1996 |
|---|---|---|
| WO | WO 99/26549 A1 | 6/1999 |

* cited by examiner

*Primary Examiner*—Tom Barrett
*Assistant Examiner*—David A. Izquierdo
(74) *Attorney, Agent, or Firm*—Thomas M. DiMauro

(57) ABSTRACT

This invention relates to a trackable medical tool for use in image guided surgery in which the drive shaft rotates about the tracking post.

29 Claims, 7 Drawing Sheets

TRACKABLE MEDICAL TOOL FOR USE IN IMAGE GUIDED SURGERY

BACKGROUND OF THE INVENTION

Computer assisted image guided medical and surgical navigation systems are known and used to generate images in order to guide a doctor during a medical procedure. See, for example, U.S. Pat. Nos. 5,769,861 & 6,428,547. Such systems frequently include a tracking array that is clamped to the instrument desired to be tracked.

U.S. Pat. No. 6,190,395 ("Williams") discloses an IGS system having a flexible clamping band used to attach the tracking array to the instrument.

U.S. Pat. No. 6,021,343 ("Foley") discloses a tool for use in image guided surgery comprising an annular guide member having a trackable array and a drive shaft for rotating an instrument such as a screwdriver while keeping the array stationary.

In each embodiment disclosed in Foley '343, the drive shaft is received within an annulus of the guide member. That is, the annulus of the guide member surrounds the drive shaft, thereby allowing the array to rotate fully around the drive shaft.

Further, Foley '343 discloses attaching the instrument to the drive shaft by a simple male-female socket, in particular a ball-and-detent mechanism. The ball and detent feature of this socket produces considerable error in tracking because the attachment occurs on one side of the connection and so is not substantially radially uniform.

SUMMARY OF THE INVENTION

The present inventors have developed a trackable medical tool wherein the tracking post component is received within a radial slot formed within the drive shaft. Therefore, in accordance with the present invention, there is provided a trackable medical tool for use in a computer assisted image guided surgery system, the instrument comprising:
  a) a longitudinal drive shaft having an outer surface having a radial slot therein, a proximal end and a distal end;
  b) a tracking post having a first end contained within the radial slot of the drive shaft;
  c) an instrument having a proximal end in connection with the distal end portion of the drive shaft; and
  d) a drive handle having a distal end in connection with the proximal end portion of the drive shaft.

In addition, the present inventors have developed a trackable medical tool wherein the coupling of the instrument to the drive shaft is provided by a means for substantially self-centered connection of the proximal end of the instrument to the distal end of the drive shaft. This self-centering means provides a more accurate tracking of the instrument because the attachment is radially uniform. Preferably, this self-centering means is provided by a collet and collet nut.

Therefore, in accordance with the present invention, there is provided a trackable medical tool for use in a computer assisted image guided surgery system, the instrument comprising:
  a) a longitudinal drive shaft having a proximal end and a distal end having a distal recess and an outer surface;
  b) a tracking device mated with the drive shaft and configured to provide at least partial rotation about the longitudinal axis of the drive shaft,
  c) a collet having a longitudinal bore defining an inner surface, a proximal outer surface contained within the distal recess of the drive shaft and a threaded distal outer surface extending from the distal recess of the drive shaft, and
  d) a collet nut having a threaded inner surface adapted to threadably mate with the threaded outer surface of the collet.

Also in accordance with the present invention, there is provided a trackable medical tool for use in a computer assisted image guided surgery system, the instrument comprising:
  a) a longitudinal drive shaft having a proximal end and a distal end having a distal recess and an outer surface;
  b) a tracking device mated with the drive shaft and configured to provide at least partial rotation about the longitudinal axis of the drive shaft,
  c) an instrument having a proximal end, and
  d) means for self-centered connection of the proximal end of the instrument to the distal end of the drive shaft.

DESCRIPTION OF THE FIGURES

FIG. 6b discloses a close-up of the intermediate portion of FIG. 6a.

DETAILED DESCRIPTION OF THE INVENTION

Preferably, the tools of the present invention are used in conjunction with a computer assisted image guided surgery system having i) a digitizer for tracking the position of the instrument in three dimensional space and ii) a display providing an indication of the position of the instrument with respect to images of a body part taken preoperatively. Preferably, the computer tracks the trajectory of the tool and the depth of the instrument inserted into the body part. In some embodiments, the computer-assisted image guided surgery system is that disclosed in U.S. Pat. Nos. 5,769,861 & 6,428,547, the specification of which is incorporated by reference.

The function of the drive shaft component of the present invention is to transmit torque from the drive handle to the instrument. Preferably, the drive shaft is fixed axially with respect to tracking post, the drive handle, and the instrument. Preferably, the drive shaft is at least partially rotatable with respect to the tracking post and stabilizer.

In preferred embodiments, the drive shaft further comprises an axial bore in communication with the slot. This bore is shaped to receive a stabilizer attached to the tracking post that helps stabilize the tracking port during rotation. Accordingly, the drive shaft is at least partially rotatable about the stabilizer.

Preferably, the slot disposed on the outer surface of the drive shaft describes an arc of between 1 degree and 270 degrees, preferably 45 degrees to 270 degrees. If the arc is less than 45 degrees, then the user needs to use the ratchet mechanism at least 8 times in order to rotate the instrument once. If the arc is greater than 270 degrees, then strength of the drive shaft may be compromised. More preferably, the arc is between 180 degrees and 270 degrees.

In preferred embodiments, the slot is disposed within the middle ⅓ of the drive shaft. This position affords the user an easy grip.

The tracking post component of the present invention provides an axially fixed connection between the array and the power train components (i.e., the drive handle, the drive shaft and the instrument). The tracking post is adapted to rotate within the slot of the drive shaft.

In preferred embodiments, a stabilizer extends from the inner end of the tracking post and is contained within the axial bore of the drive shaft. Preferably, the stabilizer extends substantially proximal from the inner end of the tracking post and terminates substantially at the proximal end of the drive shaft.

Figure 4:
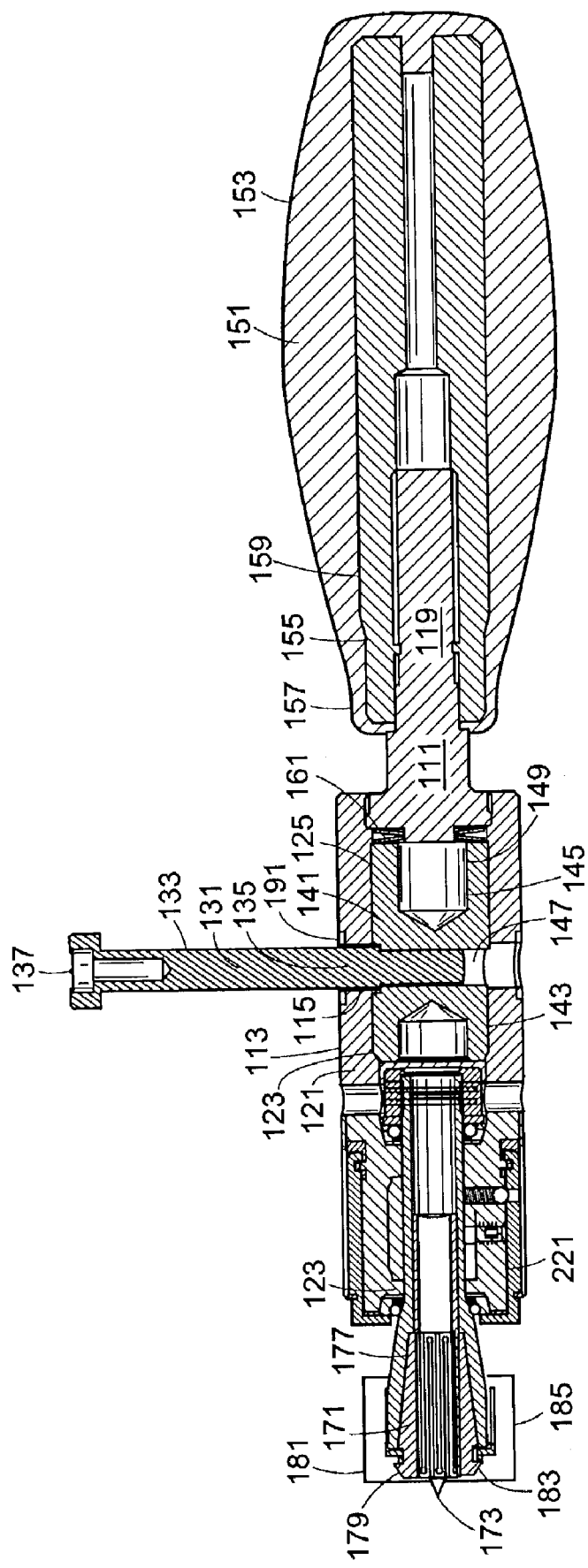
FIG. 4 discloses a cross-sectional side view of a third embodiment of the present invention.
Figure 5:
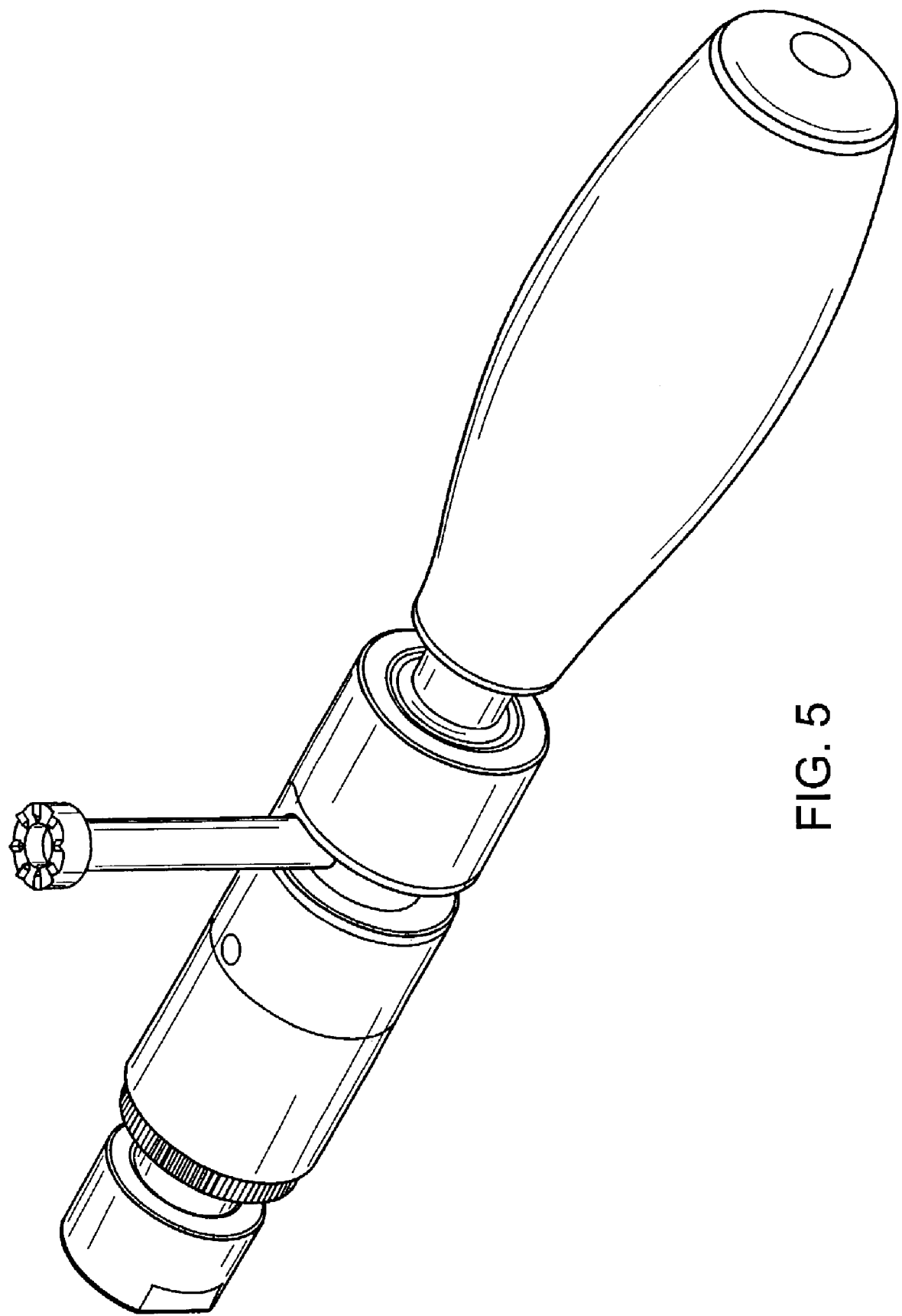
FIG. 5 discloses a perspective view of the third embodiment of the present invention.
Figure 6A:
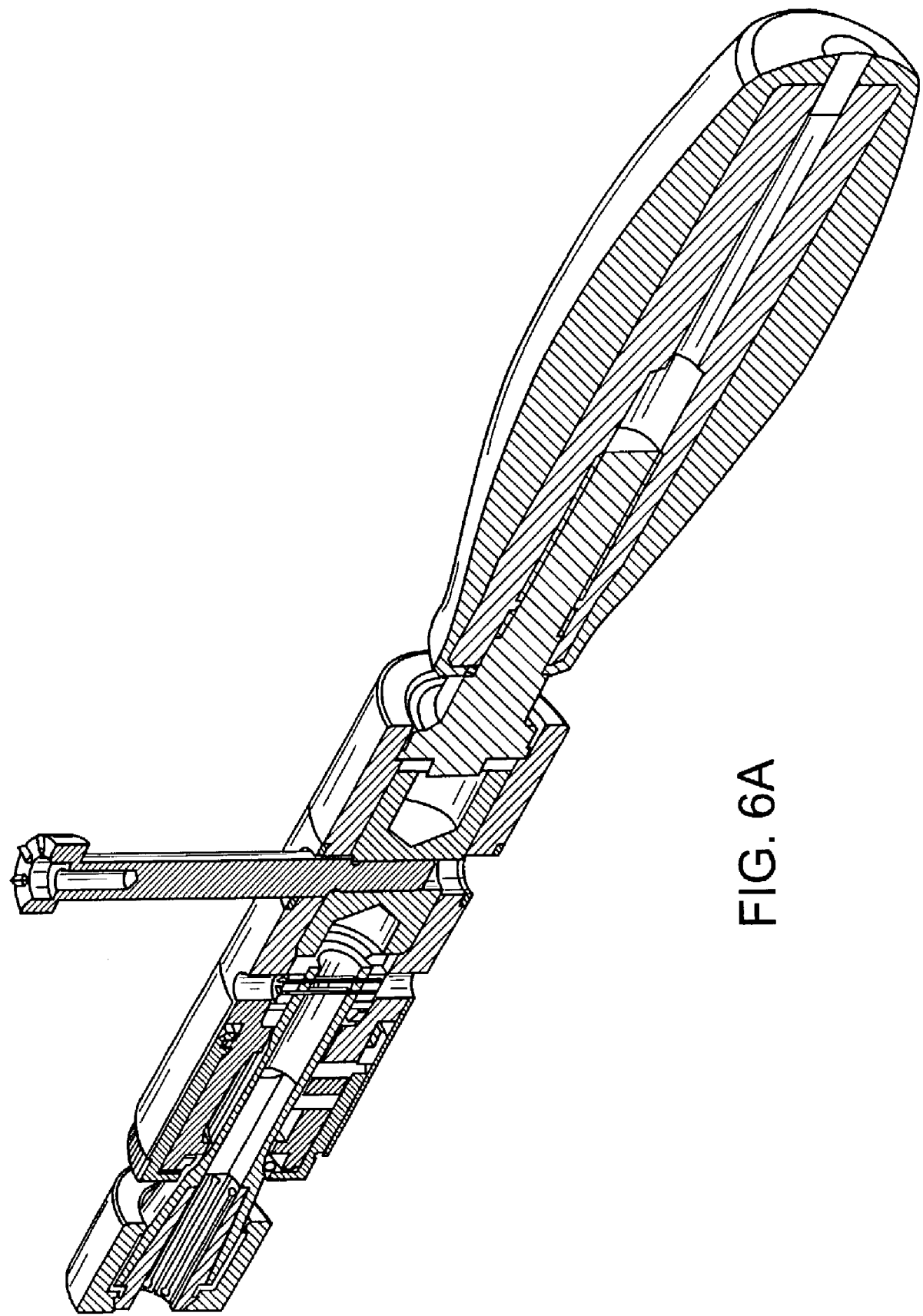
FIG. 6a disclosed a cross-sectional perspective view of a third embodiment of the present invention.
Figure 6B:
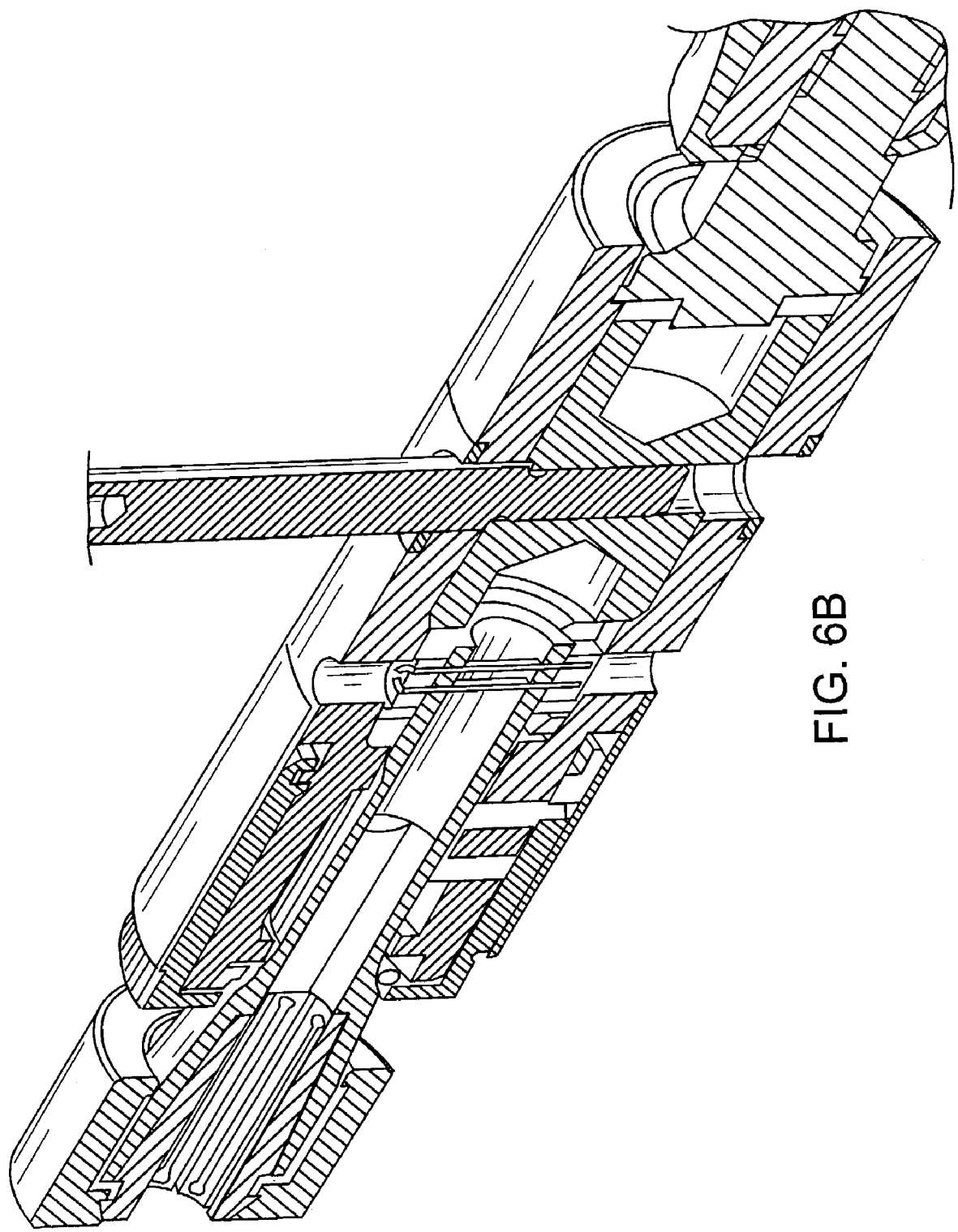

In some embodiments, now referring to FIG. 4, the tool further includes a tracking device (not shown) attached to the tracking post for tracking the location and trajectory of the instrument. The tracking device may be equipped with a plurality of tracking means, preferably three tracking means, for generating a signal representing the trajectory of the tool and the depth of the instrument tip. Preferably, the tracking means are passive, and more preferably comprise reflective surfaces. However, other tracking devices are known in the art capable of being tracked by a corresponding sensor array are within the scope of the present invention. For the purposes of illustration, and not limitation, the tracking device may generate signals actively such as with acoustic, magnetic, electromagnetic, radiologic and micropulsed systems, and emitters such as LEDs.

The instrument is located at the distal end of the tool and, when rotated, is able to work upon a body part. Preferably, the instrument rotates freely relative to the tracking post. Preferably, the instrument is axially fixed with respect to the tracking post. In some embodiments, the instrument is selected from the group consisting of a screwdriver, an awl, a tap, and a body having a shaped end for mating with a workpiece to be rotated.

The drive handle imparts rotary motion to the drive shaft and instrument. In some embodiments, the drive handle comprises a ratchet mechanism. In some embodiments, the ratchet mechanism is disposed anterior the tracking post stabilizer. In preferred embodiments, the ratchet mechanisms disclosed in U.S. Pat. Nos. 5,943,755; 5,873,288; 5,848,680; 5,778,743 and 5,771,760, the ratchet mechanism disclosures of which are incorporated by reference, are used.

Figure 1:
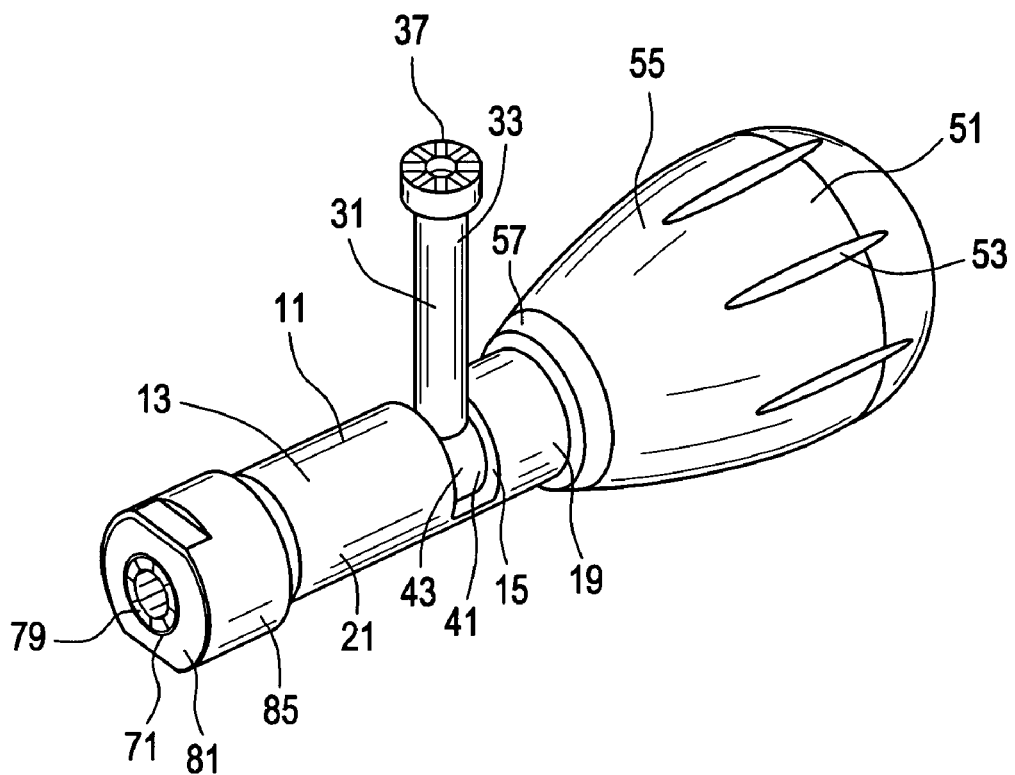
FIG. 1 discloses a perspective view of a first embodiment of the present invention showing the radial slot of the drive shaft.
Figure 2:
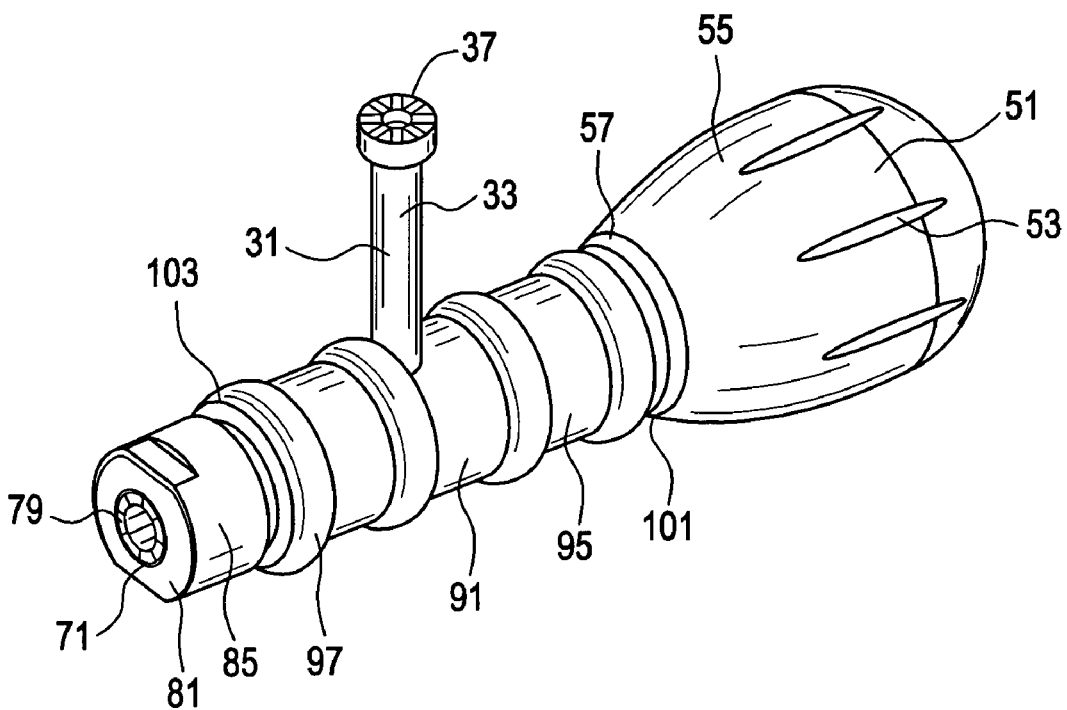
FIG. 2 discloses a perspective view of a second embodiment of the present invention having an outer guide handle.
Figure 3A:
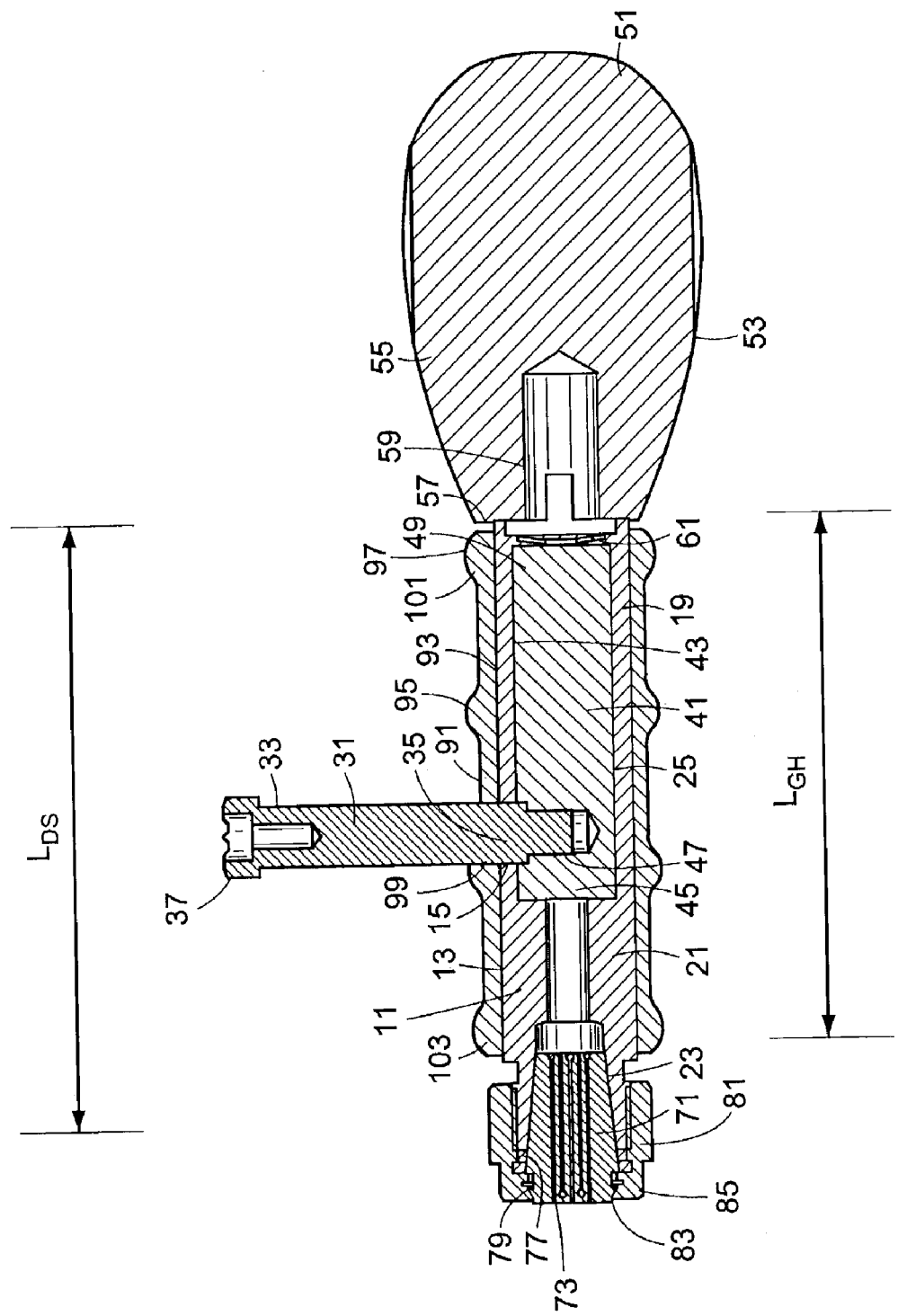
FIGS. 3a and 3b disclose cross-sectional views of the second embodiment of the present invention.
Figure 3B:
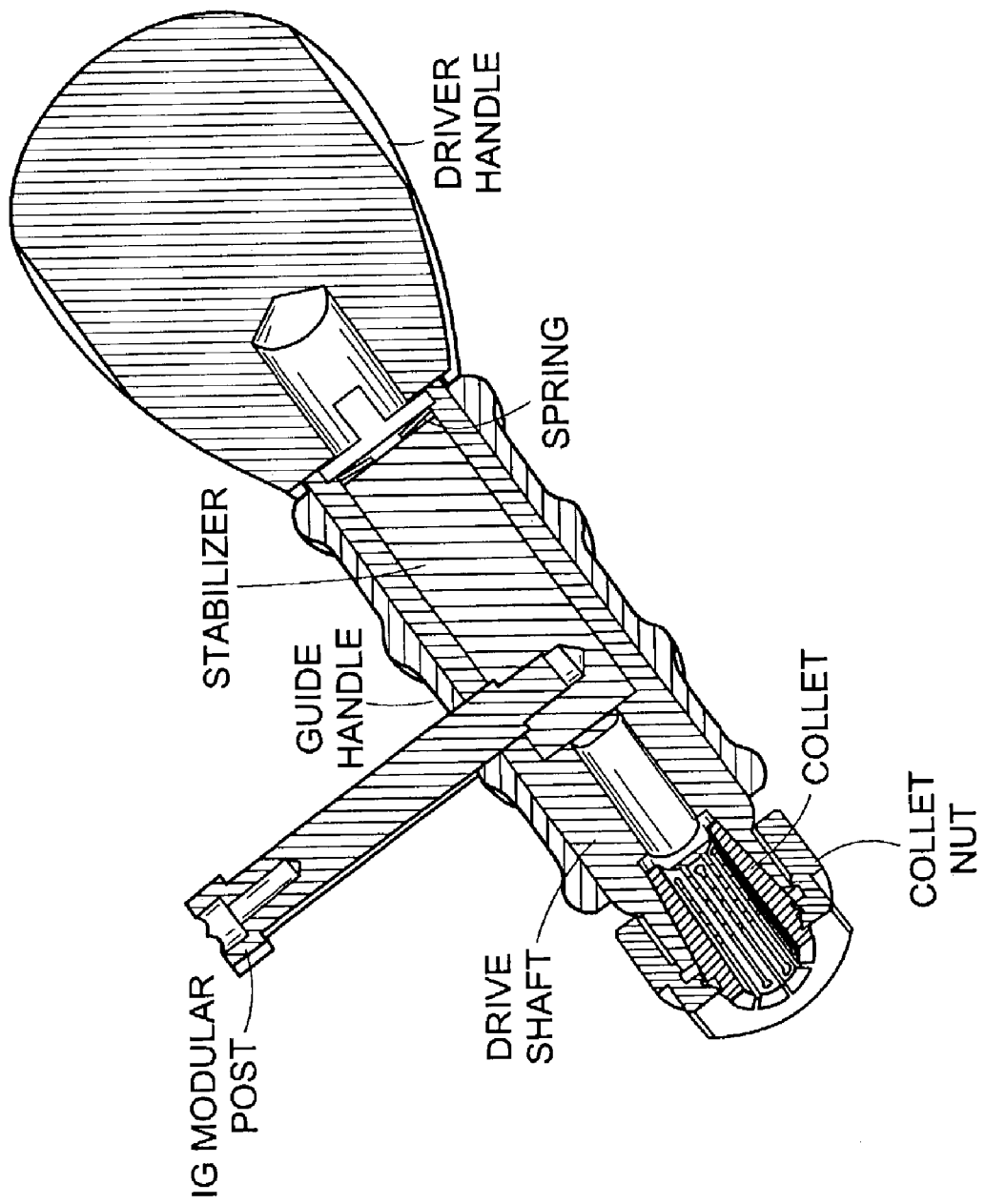

In some embodiments, the tool may further comprise a guide handle, as shown in FIG. 2. The purpose of the guide handle is to provide the user with a grippable surface for the non-dominant hand that allows the user to steady the tool while the drive handle is rotated. Preferably, the guide handle has radially extending finger grips (not shown). In some embodiments the guide handle is attached to the entire circumference of the tracking post. This circumferential attachment prevents any contamination from entering the slot of the drive shaft.

In preferred embodiments, the proximal end of the instrument is coupled to the distal end of the drive shaft by a coupling means.

Preferably, the coupling means provides a self-centered connection of the proximal end of the instrument to the distal end of the drive shaft. In some embodiments, the self-centering coupling means comprises a collet. The collet provides the user with a quick connect/disconnect option by simple hand twisting. The self-centering feature of the collet also provides a more accurate attachment of the instrument to the drive shaft than the ball-and-detent socket disclosed in the Foley '343 patent. In some embodiments, the coupling means comprises a collet, a collet chuck and a collet nut. Preferably, the instrument is inserted through the collet and into the collet chuck. In some embodiments, the transverse cross-section of the distal end of the collet chuck recess has a non-circular shape, such as a D-shaped drive feature. This feature provides enhanced torque transmission.

In other embodiments, the coupling means may be a Hudson connection.

In some embodiments, the tool further comprises a lock. The lock prevents rotation of the drive handle vis-a-vis the guide handle, and so would be desirable when the surgeon is using a non-rotating instrument such as an awl. This lock may be provided by an external latch connecting the drive handle and guide handle, or by internally enclosed ratchet mechanisms.

Now referring to FIGS. 1–3b, there is provided a trackable medical tool for use in a computer assisted image guided surgery system, the instrument comprising:

a) a longitudinal drive shaft 11 having an outer surface 13 having a radial slot 15 therein forming a cavity, a proximal end portion 19, a distal end portion 21 having a distal recess 23 therein, an inner surface 25 forming a longitudinal inner bore communicating with the cavity and extending to the proximal end, the distal end and the proximal end forming a length $L_{DS}$;

b) a tracking post 31 having an outer surface 33, an inner end 35 contained within the slot, and an outer end 37 adapted to receive an array;

c) a stabilizer 41 having an outer surface 43 contained within the inner bore of the drive shaft, a distal end portion 45 having a recess 47 adapted to receive the inner end of the tracking post, and a proximal end portion 49;

d) a drive handle 51 having an outer surface 53 adapted for gripping, a distal end 55 having an outer portion 57 attached to the proximal end portion of the drive shaft and an inner portion 59;

e) a spring 61 having a distal portion abutting the proximal portion of the stabilizer and a proximal portion abutting the inner distal portion of the drive handle;

f) a collet 71 having a longitudinal bore 73 defining an inner surface, a proximal outer surface 77 contained within the distal recess of the drive shaft, and a threaded distal outer surface 79 extending from the distal recess of the drive shaft;

g) a collet nut 81 having a threaded inner surface 83 threadably mating with the threaded distal outer surface of the collet and an outer surface 85 adapted for gripping;

h) an annular guide handle 91 having an inner surface 93 rotatably receiving the outer surface of the drive shaft, an outer surface 95 having a plurality of raised radial ridges 97, and a throughhole 99 extending from the inner surface to the outer surface forming an attachment surface, and a proximal end 101 and a distal end 103 forming a length $L_{GH}$, wherein the tracking post is received in the through-hole of the annular guide handle and a portion of the outer surface of the tracking post is rigidly connected to the attachment surface of the annular guide handle;

i) a lock (not shown) adapted for selectively preventing rotation of the drive shaft relative to the drive handle, j) an instrument (not shown) having a proximal end portion received within the inner surface of the collet, a longitudinal intermediate shaft portion, and a distal working portion, and k) a ratchet mechanism (not shown) for adapted for ratchet-like rotation of the drive shaft relative to the drive handle.

Now referring to FIGS. 4–6b, there is provided a trackable medical tool for use in a computer assisted image guided surgery system, the instrument comprising:

a) a longitudinal drive shaft 111 having an outer surface 113 having a radial slot 115 therein forming a cavity, a proximal end portion 119, a distal end portion 121 having a distal recess 123 therein, an inner surface 125 forming a longitudinal inner bore communicating with the cavity and extending towards the proximal end;

b) a tracking post 131 having an outer surface 133, an inner end 135 contained within the slot, and an outer end 137 adapted to receive an array, wherein the tracking post is received in the slot of the drive shaft;

c) a stabilizer 141 having an outer surface 143 contained within the inner bore of the drive shaft, a distal end portion 145 having a recess 147 adapted to receive the inner end of the tracking post, and a proximal end portion 149;

d) a drive handle 151 having an outer surface 153 adapted for gripping, a distal end 155 having an outer portion 157 attached to the proximal end portion of the drive shaft and an inner portion 159;

e) a spring 161 having a distal portion abutting the proximal portion of the stabilizer and a proximal portion abutting the inner distal portion of the drive handle;

f) a collet 171 having a longitudinal bore 173 defining an inner surface, a proximal outer surface 177 contained within the distal recess of the drive shaft, and a threaded distal outer surface 179 extending from the distal recess of the drive shaft;

g) a collet nut 181 having a threaded inner surface 183 threadably mating with the threaded distal outer surface of the collet and an outer surface 185 adapted for gripping;

h) a silicon cover member 191 having an inner surface fixedly received upon the outer surface of the drive shaft and around the slot the drive shaft, and a through-hole formed around the slot for receiving the tracking post, i) a lock (not shown) adapted for selectively preventing rotation of the drive shaft relative to the handle, j) an instrument (not shown) having a proximal end portion received within the inner surface of the collet, a longitudinal intermediate shaft portion, and a distal working portion, and k) a ratchet mechanism 221 for adapted for ratchet-like rotation of the drive shaft relative to the drive handle.

The function of the tool of the present invention is to help the surgeon track the trajectory of a surgical instrument placed within the body, thereby enhancing the access and accuracy of the spinal surgery procedure. Preferably, the selected instrument can mark, puncture, probe, tap, screw or guide the placement of an implant. Instruments are attached to the tool of the present invention by placing the proximal end of the instrument into the centering distal coupling means and preferably piloting the proximal end into the recessed 'D' feature of the collet chuck for increased torque. Rotation of the collet nut component of the coupling means centers and secures the instrument. The ratchet mechanism is then adjusted to select rotation options such as non-rotation, right hand drive and left handed drive.

When used with image guided surgery, the tool of the present invention is registered with an image guided surgery system to determine the trajectory and position of the instrument relative to the tracking array. This trajectory can be determined with preoperative CT or other imaging data to provide an operative display of instrument with bony tissue.

A preferred method with rotary drive instruments (tap or screw) comprises the steps of placing the surgeon's dominant hand on the proximal drive handle and the surgeon's non-dominant hand on the distal portion of the drive shaft, with the tracking post typically help upright between the surgeon's fingers. Rotation is applied to the drive handle with dominant hand while non-dominant hand stabilizes the drive shaft. As rotation is imparted, the drive shaft rotates around the stabilizer and torque is transferred through the ratchet drive mechanism to the instrument. Rotation of the dominate handle in the opposite direction activates the ratchet mechanism to allow the drive handle to return to its original position and to provide smooth advancement of the surgical instrument while trajectory image is displayed operatively.

Typically, the components of the present invention can be made out of any material commonly used in medical instruments. If the device is designed to be reusable, it is preferred that all the components be made of stainless steel. If the device is designed to be disposable, it is preferred that some of the components be made of plastic. Preferably, at least one component is sterilized. More preferably, each component is sterilized.

In some embodiments, the body part upon which the tool of the present invention works is hard tissue. In preferred embodiments, the hard tissue comprises bone. In more preferred embodiments, the body part is a human vertebra. In more preferred embodiments, the tool works upon the posterior portion of the vertebra.

We claim:

1. A trackable medical tool for use in a computer assisted image guided surgery system, the instrument comprising:

a) a longitudinal drive shaft having an outer surface having a radial slot therein, a proximal end and a distal end;

b) a tracking post having a first end contained within the radial slot of the drive shaft;

c) an instrument having a proximal end in connection with the distal end portion of the drive shaft; and d) a drive handle having a distal end in connection with the proximal end portion of the drive shaft, wherein a bore is shaped to receive a stabilizer attached to the tracking post that helps stabilize the tracking post during rotation, wherein the drive shaft is at least partially rotatable about the stabilizer.

2. The tool of claim 1 wherein the drive shaft is at least partially rotatable with respect to the tracking post.

3. The tool of claim 1 wherein the drive shaft farther comprises an axial bore in communication with the slot.

4. The tool of claim 1 wherein the slot disposed on the outer surface of the drive shaft describes an arc of between 45 degrees and 270 degrees.

5. The tool of claim 1 wherein the slot is disposed within the middle ⅓ of the drive shaft.

6. The tool of claim 1 wherein the tracking post further comprises an outer end adapted to receive a tracking means.

7. The tool of claim 1 wherein all the components be made of stainless steel.

8. The tool of claim 1 wherein at least one component is sterilized.

9. The tool of claim 1 wherein each component is sterilized.

10. The tool of claim 1 wherein the instrument is adapted for use upon hard tissue.

11. The tool of claim 10 wherein the hard tissue is the posterior portion of the vertebra.

12. The tool of claim 1 wherein the hard tissue comprises bone.

13. The tool of claim 12 wherein bone is a human vertebra.

14. A trackable medical tool for use in a computer assisted image guided surgery system, the instrument comprising:
 a) a longitudinal drive shaft having an outer surface having a radial slot therein, a proximal end and a distal end;
 b) a tracking post having a first end contained within the radial slot of the drive shaft;
 c) an instrument having a proximal end in connection with the distal end portion of the drive shaft; and
 d) a drive handle having a distal end in connection with the proximal end portion of the drive shaft,
 wherein the tracking post further comprised a stabilizer extending from an inner end of the tracking post and contained within an axial bore of the drive shaft.

15. The tool of claim 14 wherein the stabilizer extends substantially proximal from the inner end of the tracking post and terminates substantially at the proximal end of the drive shaft.

16. A trackable medical tool for use in a computer assisted image guided surgery system, the instrument comprising:
 a) a longitudinal drive shaft having an outer surface having a radial slot therein, a proximal end and a distal end;
 b) a tracking post having a first end contained within the radial slot of the drive shaft;
 c) an instrument having a proximal end in connection with the distal end portion of the drive shaft; and
 d) a drive handle having a distal end in connection with the proximal end portion of the drive shaft,
further comprising
 e) a tracking device attached to tracking post for tracking the location and trajectory of the instrument.

17. The tool of claim 16 wherein the tracking device comprises a plurality of tracking means for generating a signal representing the trajectory of the tool and the depth of the instrument tip.

18. The tool of claim 17 wherein the tracking means are passive.

19. The tool of claim 18 wherein the passive tracking means comprises reflective surfaces.

20. The tool of claim 17 wherein the tracking device is selected from the group consisting of an acoustic system, a magnetic system, an electromagnetic system, a radiologic system and a micropulsed system, and an emitter.

21. The tool of claim 1 wherein the instrument is axially fixed with respect to the tracking post.

22. The tool of claim 1 wherein the instrument is selected from the group consisting of a screwdriver, an awl, a tap, and a body having a shaped end for mating with a workpiece to be rotated.

23. A trackable medical tool for use in a computer assisted image guided surgery system, the instrument comprising:
 a) a longitudinal drive shaft having an outer surface having a radial slot therein, a proximal end and a distal end;
 b) a tracking post having a first end contained within the radial slot of the drive shaft;
 c) an instrument having a proximal end in connection with the distal end portion of the drive shaft; and
 d) a drive handle having a distal end in connection with the proximal end portion of the drive shaft,
 wherein the drive shaft comprises a ratchet mechanism.

24. A trackable medical tool for use in a computer assisted image guided surgery system, the instrument comprising:
 a) a longitudinal drive shaft having an outer surface having a radial slot therein, a proximal end and a distal end;
 b) a tracking post having a first end contained within the radial slot of the drive shaft;
 c) an instrument having a proximal end in connection with the distal end portion of the drive shaft; and
 d) a drive handle having a distal end in connection with the proximal end portion of the drive shaft,
 wherein the proximal end of the instrument is coupled to the distal end of the drive shaft by a coupling means, wherein the coupling means comprises a collet.

25. The tool of claim 24 wherein the collet has a longitudinal bore defining an inner surface, a proximal outer surface contained within the distal recess of the drive shaft with a threaded distal outer surface extending from the distal recess of the drive shaft.

26. The tool of claim 25 wherein the coupling means farther comprises a collet nut having a threaded inner surface adapted to threadably mate with the threaded outer surface of the collet.

27. A trackable medical tool for use in a computer assisted image guided surgery system, the instrument comprising:
 a) a longitudinal drive shaft having an outer surface having a radial slot therein, a proximal end and a distal end;
 b) a tracking post having a first end contained within the radial slot of the drive shaft;
 c) an instrument having a proximal end in connection with the distal end portion of the drive shaft; and
 d) a drive handle having a distal end in connection with the proximal end portion of the drive shaft,
 wherein a computer has a digitizer for tracking the position in three dimensional space.

28. The tool of claim 27 wherein the computer further comprises a display providing an indication of the position of the instrument with respect to images of a body part taken preoperatively.

29. The tool of claim 28 wherein the computer is adapted to track the trajectory of the tool and the depth of the instrument inserted into the body part.

* * * * *